United States Patent
Anderson et al.

(10) Patent No.: US 6,210,364 B1
(45) Date of Patent: Apr. 3, 2001

(54) DISTENSIBLE DILATATION BALLOON WITH ELASTIC STRESS RESPONSE

(75) Inventors: Jere R. Anderson, Newburyport; Louis J. Jandris, Georgetown; Michael D. Barbere, Dunstable; Richard T. Murphy, Dracut, all of MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 08/883,261

(22) Filed: Jun. 26, 1997

(Under 37 CFR 1.47)

Related U.S. Application Data

(60) Continuation of application No. 08/440,700, filed on May 15, 1995, now abandoned, which is a division of application No. 07/954,750, filed on Sep. 30, 1992, now Pat. No. 5,500,180.

(51) Int. Cl.⁷ .................................................. A61M 29/00
(52) U.S. Cl. .................. 604/96.01; 604/103.06; 604/915; 606/192
(58) Field of Search ............. 604/96.01, 103.06, 604/103.11–103.13, 915; 606/192, 194

(56) References Cited

U.S. PATENT DOCUMENTS

| | | |
|---|---|---|
| Re. 32,983 | 7/1989 | Levy .................................. 428/36.92 |
| 3,754,851 | 8/1973 | Reilly et al. . |
| 4,003,383 | 1/1977 | Dyke .................................. 128/349 B |
| 4,154,244 | 5/1979 | Becker et al. ......................... 604/96 |
| 4,331,786 | 5/1982 | Foy et al. . |
| 4,376,334 | 3/1983 | Goldwasser et al. ................. 521/159 |
| 4,385,089 | 5/1983 | Bonnebat et al. .................... 264/528 |
| 4,385,635 | 5/1983 | Ruiz . |
| 4,413,989 | 11/1983 | Schjeldahl et al. . |
| 4,448,195 | 5/1984 | LeVeen et al. ....................... 128/344 |
| 4,456,011 | 6/1984 | Warnecke ............................ 128/325 |
| 4,481,323 | 11/1984 | Sterling .................................. 604/96 |
| 4,482,518 | 11/1984 | Brady, Jr. . |
| 4,490,421 | 12/1984 | Levy . |
| 4,528,343 | 7/1985 | Kira . |
| 4,623,347 | 11/1986 | Kira . |
| 4,675,361 | 6/1987 | Ward, Jr. . |
| 4,722,344 | 2/1988 | Cambron et al. . |
| 4,786,556 | 11/1988 | Hu et al. . |
| 4,820,349 | 4/1989 | Saab . |
| 4,861,830 | 8/1989 | Ward, Jr. . |
| 4,886,506 | 12/1989 | Lovgren et al. . |
| 4,898,591 | 2/1990 | Jang et al. . |
| 4,906,244 | 3/1990 | Pinchuk et al. ....................... 606/194 |
| 4,917,667 | 4/1990 | Jackson . |
| 4,938,676 | 7/1990 | Jackowski et al. ................... 264/530 |

(List continued on next page.)

FOREIGN PATENT DOCUMENTS

| | | |
|---|---|---|
| 0439202 | 7/1991 | (EP) . |
| 0485903 | 5/1992 | (EP) . |
| WO 9001302 | 2/1990 | (WO) . |
| WO 9117788 | 11/1991 | (WO) . |
| 9509667 | 4/1995 | (WO) . |
| 9523619 | 9/1995 | (WO) . |

OTHER PUBLICATIONS

In–Mold Anneal, Research Disclosure, Mar. 1975, pp. 58–59 (cited in parent application Serial No. 07/954,750, now U.S. 5,500,180).

*Primary Examiner*—Wynn Wood Coggins
*Assistant Examiner*—Cris L. Rodriguez

(57) ABSTRACT

Balloons and balloon catheters with superior overall combination of distensibility, elastic stress response and strength. The improved properties of a balloons result from the method or process used to form the balloons, as well as the polymeric materials used in said balloon forming process. Additionally, the enhanced combination of properties of the balloons will not be adversely affected by the novel sterilization process contemplated by this invention.

14 Claims, 3 Drawing Sheets

U.S. PATENT DOCUMENTS

| | | |
|---|---|---|
| 4,950,239 | 8/1990 | Gahara et al. .................. 604/96 |
| 4,950,257 | 8/1990 | Hibbs et al. . |
| 4,952,357 | 8/1990 | Euteneuer . |
| 4,963,313 | 10/1990 | Noddin et al. . |
| 5,017,325 | 5/1991 | Jackowski et al. . |
| 5,055,024 | 10/1991 | Jackowski et al. . |
| 5,087,394 | 2/1992 | Keith . |
| 5,108,415 | 4/1992 | Pinchuk et al. . |
| 5,156,612 | 10/1992 | Pinchuk et al. . |
| 5,169,464 | 12/1992 | Foldesy et al. ................ 264/564 |
| 5,192,296 | 3/1993 | Bhate et al. . |
| 5,195,970 | 3/1993 | Gahara . |
| 5,223,205 | 6/1993 | Jackowski et al. . |
| 5,236,659 | 8/1993 | Pinchuk et al. . |
| 5,250,069 | 10/1993 | Nobuyoshi et al. . |
| 5,257,974 | 11/1993 | Cox . |
| 5,264,260 | 11/1993 | Saab . |
| 5,281,677 | 1/1994 | Onwunaka et al. . |
| 5,290,306 | 3/1994 | Trotta et al. . |
| 5,295,978 | 3/1994 | Fan et al. . |
| 5,300,048 | 4/1994 | Drewes, Jr. et al. . |
| 5,304,134 | 4/1994 | Kraus et al. . |
| 5,304,340 | 4/1994 | Downey . |
| 5,328,468 | 7/1994 | Kaneko et al. . |
| 5,334,146 | 8/1994 | Ozasa . |
| 5,335,675 | 8/1994 | Wheeler et al. . |
| 5,342,301 | 8/1994 | Saab . |
| 5,342,305 | 8/1994 | Shonk . |
| 5,344,400 | 9/1994 | Kaneko et al. . |
| 5,344,401 | 9/1994 | Radisch . |
| 5,348,486 | 9/1994 | Saab . |
| 5,348,538 | 9/1994 | Wang et al. ................... 604/96 |
| 5,387,199 * | 2/1995 | Siman et al. .................. 604/282 |
| 5,397,306 | 3/1995 | Nobuyoshi et al. . |
| 5,403,340 | 4/1995 | Wang et al. ................... 606/194 |
| 5,447,497 | 9/1995 | Sogard et al. .................. 604/101 |
| 5,500,181 | 3/1996 | Wang et al. . |
| 5,556,383 * | 9/1996 | Wang et al. ................... 604/96 |

\* cited by examiner

DISTENSIBLE DILATATION BALLOON WITH ELASTIC STRESS RESPONSE

This application is a continuation, of application No. 08/440,700 filed May 15, 1995, now abandoned, which is a divisional of application No. 07/954,750 filed Sep. 30, 1992, now U.S. Pat. No. 5,500,180.

BACKGROUND OF INVENTION

Surgical procedures employing balloons and medical devices incorporating those balloons (i.e., balloon catheters) are becoming more common and routine. These procedures, such as angioplasty procedures, are conducted when it becomes necessary to expand or open narrow or obstructed openings in blood vessels and other passageways in the body to increase the flow through the obstructed areas. For example, in an angioplasty procedure, a dilatation balloon catheter is used to enlarge or open an occluded blood vessel which is partially restricted or obstructed due to the existence of a hardened stenosis or buildup within the vessel. This procedure requires that a balloon catheter be inserted into the patient's body and positioned within the vessel so that the balloon, when inflated, will dilate the side of the obstruction or stenosis so that the obstruction or stenosis is minimized, thereby resulting in increased blood flow through the vessel. Often, however, a stenosis requires treatment with multiple balloon inflations. Additionally, many times there are multiple stenosis within the same vessel or artery. Such conditions require that either the same dilatation balloon must be subjected to separated inflations, or that multiple dilatation balloons must be used to treat an individual stenosis or the multiple stenosis within the same vessel or artery. Additionally, balloons and medical devices incorporating those balloons may also be used to administer drug to a patient.

Traditionally, the balloons available to physicians were classified as either "complaint" or "noncomplaint". This classification is based upon the operating characteristics of the individual balloon, which in turn depended upon the process used in forming the balloon, as well as the material used in the balloon forming process. Both types of balloons provide advantageous qualities which were not available from the other.

A balloon which is classified as "noncomplaint" is characterized by the balloon's inability to grow or expand appreciably beyond its rated or nominal diameter. "Non-complaint" balloons are referred to as having minimal distensibility. In balloons currently known in the art (e.g., polyethylene terephthalate), this minimal distensibility results from the strength and rigidity of the molecular chains which make up the base polymer, as well as the orientation and structure of those chains resulting from the balloon formation process. The strength resulting from this highly oriented structure is so great that when the balloon is subjected typical inflation or operating pressures (i.e., about 70 psi to over 200 psi), it will not be stressed above the yield point of the polymeric material.

The yield point of a material is defined as the stress at which the individual molecular chains move in relations to one another such that when the pressure or stress is relieved, there is permanent deformation of the structure. When a material is subjected to pressure or stress below its yield point, the material will consistently follow the same stress-strain curve when subjected to multiple cycles of applying and relieving the stress or pressure. A material which exhibits the ability to follow the same stress-strain curve during the repeated application and relief of stress is defined as being elastic and as having a high degree of elastic stress response. This elastic behavior is highly desirable in balloons in order to ensure consistent and predictable balloon sizing regardless of the balloon's previous inflation history.

A balloon which is referred to as being "compliant" is characterized by the balloon's ability to grow or expand beyond its nominal or rated diameter. In balloons currently known in the art (e.g., polyethylene, polyvinylchloride), the balloon's "compliant" nature or distensibility results from the chemical structure of the polymeric material used in the formation of the balloon, as well as the balloon forming process. These polymeric materials have a relatively low yield point. Thus, the inflation pressures used in dilation procedures are typically above the yield point of the materials used to form distensible balloons. A distensible or "compliant" balloon when inflated to normal operating pressures, which are greater than the polymeric material's yield point, is subjected to stress sufficient to permanently realign the individual molecular chains of the polymeric material. The realignment of individual polymer chains permits the balloon to expand beyond its nominal or rated diameter. However, since this realignment is permanent, the balloon will not follow its original stress-strain curve on subsequent inflation-deflation cycles. Therefore, the balloon balloon upon subsequent inflations, will achieve diameters which are greater than the diameters which were originally obtained at any given pressure during the course of the balloon's initial inflation.

The term "elastic", as it is used in connection with this invention, refers only to the ability of a material to follow the same stress-strain curve upon the multiple applications of stress. See Beer, F. et al., *Mechanics of Materials* (McGraw-Hill Book Company 1981), pp. 39–40. Elasticity, however, is not necessarily a function of how distensible a material is. It is possible to have an elastic, non-distensible material or a non-elastic, distensible material. This is best illustrated in FIG. 1, 2 and 3.

BRIEF DESCRIPTION OF THE DRAWINGS

FIG. 3 shows a significant change in strain (diameter) and would therefore be considered a distensible balloon material. Unlike FIGS. 1 and 2, however, the same stress-strain (pressure-diameter) curve is not maintained upon the second application of stress (inflation).

Figure 1:
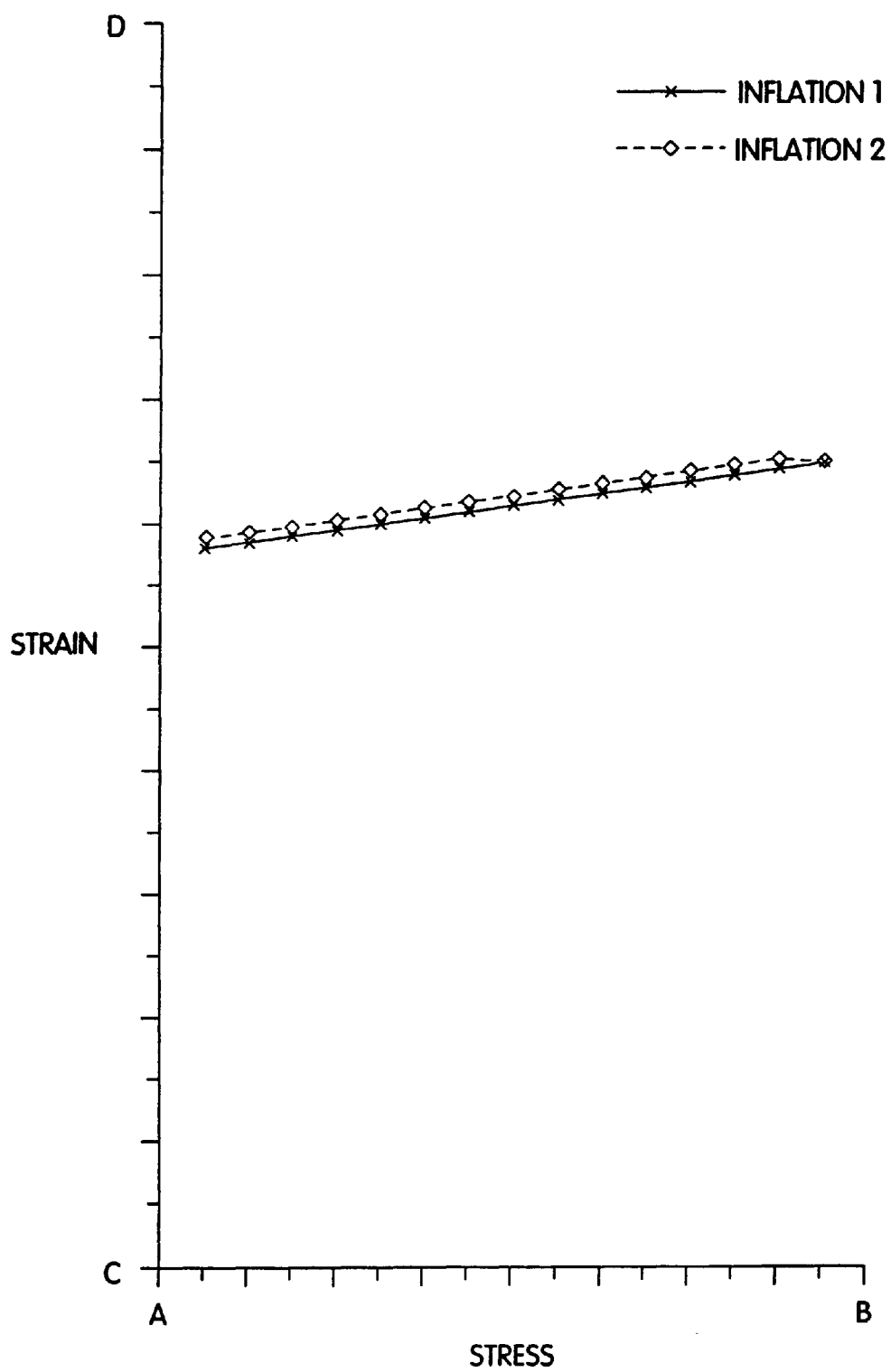
FIG. 1 represents an elastic, essentially non-distensible material. If this material was used to form a balloon, the balloon would be considered non-distensible because there is very little change in strain (diameter) as the stress applied is increased (inflation pressure). The balloon would be elastic because it follows essentially the same stress-strain (pressure-diameter) curve with the second application of stress (inflation).
Figure 2:
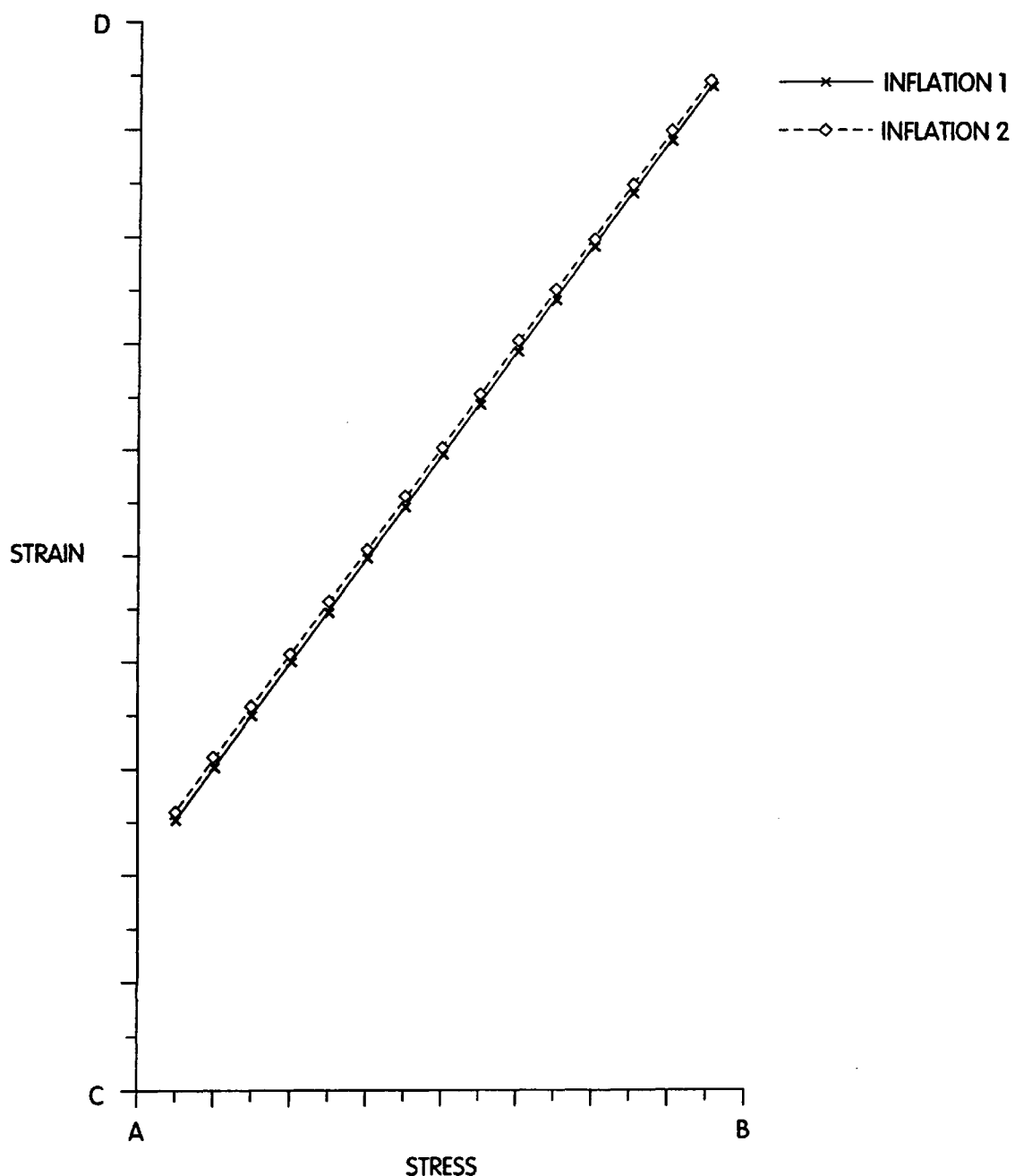
FIG. 2 represents an elastic, distensible material. If this material was used to form a balloon, the balloon would be considered distensible because there is significant change in strain (diameter) as the stress applied is increased (inflation pressure). The balloon would be considered elastic because it follows essentially the same stress-strain (pressure-diameter) curve with the second application of stress (inflation).
Figure 3:
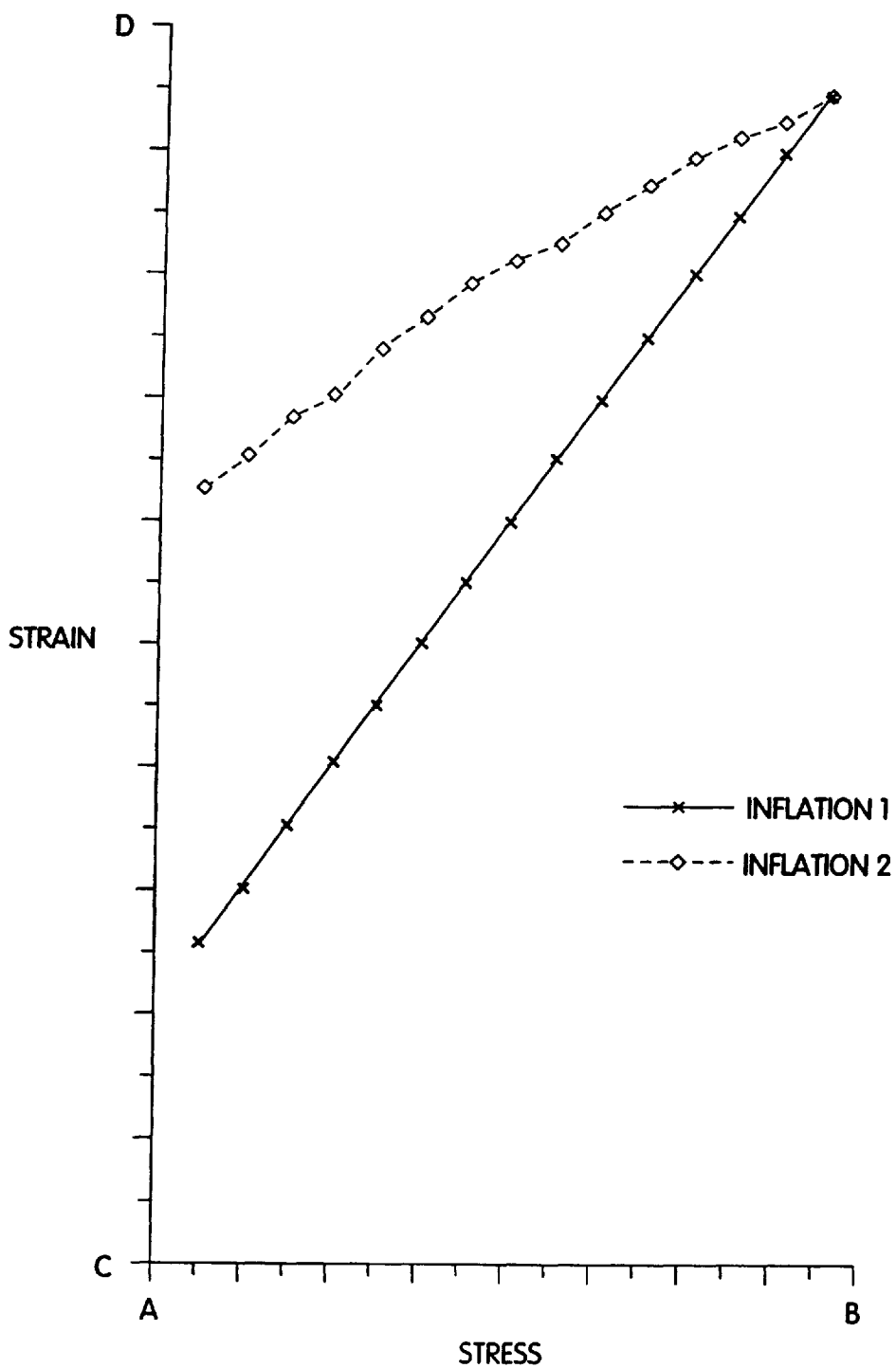
FIG. 3 represents an inelastic, distensible material. Like FIG. 2.

It has been found that the optimal size of a dilatation balloon is about 0.9 to about 1.3 the size of the vessel being treated. See Nichols et al., *Importance of Balloon Size in Coronary Angioplasty*, J. American College of Cardiology, Vol. 13, 1094 (1989). If an undersized balloon is used, there is a high incidence of significant residual stenosis and a greater need for subsequent dilatation procedures. However, if an oversized balloon is used, there is an increased chance of coronary dissecting. Therefore, physicians desire to use a balloon which will closely approximate the size of the occluded vessel or obstructed cavity being treated.

Because physiological vessels such as arteries are generally tapered, the nominal or rate diameter of balloons commercially available often do not correspond to the size of the vessel being treated. Physicians, therefore, are often faced with the prospect of using an undersized "complaint" balloon which can be expanded beyond its nominal or rated diameter, or an oversized "noncompliant" balloon which will follow the same stress-strain curve during multiple inflations (i.e., is elastic). Thus, physicians can choose from two general types of balloons depending upon whether they require a balloon which grows beyond nominal diameter. They may choose a "noncomplaint" balloon if they require a relatively high strength balloon which will not expand much beyond its nominal or rated diameter, or a "compliant" balloon if they require a balloon which is capable of expanding considerably beyond the normal or rated diameter. As will be shown below, each of these properties is advantageous. However, it would be desirable to have to have a "compliant" or distensible balloon which also has the elastic stress response of a "noncompliant" balloon, as well as sufficient strength to be used in dilatation procedures.

Because physicians using a dilatation balloon do not know prior to the procedure what inflation pressures will be required to dilate a given obstruction or stenosis, it is desirable that the balloon being used have strength capable of withstanding the high inflation pressures typically associated with these procedures (i.e., about 70 to over 200 psi). A high strength dilatation balloon, which is capable of withstanding increased inflation pressure, is safer to use since the chances of the balloon bursting during the procedure are minimized.

Strength of a balloon is typically quantified by calculating the balloon's wall tensile strength. The overall strength of a balloon can be increased by increasing the balloon's wall thickness. As the wall thickness is increased, the balloon is capable of withstanding higher inflation pressures. However, as the wall thickness of the balloon is increased, the folded profile of the balloon, as well as the balloon's flexibility, may be adversely affected.

The relationship between the ultimate strength of the balloon, the inflation pressure which the balloon can withstand and the balloon's wall thickness is determined by the well known membrane equation:

$$\text{Wall Tensile Strength } (psi) = \frac{(\text{burst pressure }(psi)) \times (\text{nominal balloon diameter})}{2 \times (\text{wall thickness})}$$

Depending upon the material used to form the balloon, the nominal, or rated diameter is achieved typically when the balloon is inflated between to about 5 bars to about 8 bars. The burst pressure is determined at 37° C.

Since balloons, particularly dilatation balloons, must have the ability to transverse the confines of the obstructed areas to be treated, it is desirable to have a balloon which has a narrow folded profile. This "profile" represents the smallest opening through which the balloon, in its deflated state, may pass. The profile of the balloon depends in large part upon the wall thickness of the finished balloon (i.e., the sterilized dilatation balloon product). Therefore, it is desirable for a finished balloon product to have a folded profile which is as narrow as possible, particularly if the balloon is to be used in an angioplasty procedure.

Another important characteristic of balloons in general, and more specifically dilatation balloons, is the distensibility of the finished balloon product. Distensibility, also referred to as percent of radial expansion, is typically determined by comparing the nominal or rated diameter of the balloon with the diameter at some arbitrarily selected higher pressure (e.g., 10 bars). The distensibility or percent radial expansion is calculated using the following formula with all measurements taking place at about 37° C.:

$$\text{Distensibility} = \left[ \frac{\text{Diameter of balloon at 10 bars}}{\text{Nominal balloon diameter}} - 1 \right] \times 100\%$$

For example, balloon made of polyethylene terephthalate have a low distensibility (i.e., less than about 5% at 200 psi). See for example U.S. Pat. Nos. Re. 32,983 and 33,561 to Levy which discloses balloon formed from polyethylene terephthalate and other polymeric materials.

It is also desirable that the balloon be elastic or have a high degree of elastic stress response. Elasticity, which also can be referred to as the repeatability of a balloon, is characterized by the ability of the balloon to consistently follow the same stress-strain curve after being subjected to multiple inflations to normal operating or inflation pressures (i.e., about 10 bars or greater). That is, a balloon which has a high degree of elastic stress response will retain the same diameter-pressure relationship and will consistently obtain the same diameter at the same pressure during repeated inflation-deflation cycles. Balloons which have poor elasticity or a low degree of elastic stress response have a tendency to "creep" or "deform" after multiple inflations and fail to return to their nominal or rated diameters after being subjected to multiple inflations at increased pressures.

A dilatation balloon which has a high degree of elastic stress response is particularly desirable when a physician is treating multiple stenosis within the same artery. If the balloon is "inelastic", after the first stenosis is dilated at an increased pressure, the physician would not known what the balloon's "new" starting diameter is prior to attempting to dilate subsequent stenosis. If the physician fails to correctly guess the balloon's "new" diameter prior to beginning treatment of another stenosis there is an increased risk of oversizing the balloon which could result in coronary artery dissection or other damage to the vessel. Therefore, to ensure the patient's safety, some physicians elect to remove the balloon catheter from the patient and reintroduce a new sterile balloon catheter prior to attempting to dilate subsequent stenosis within the same vessel. However, this is time-consuming and undesirable for the patient. Additionally, the cost of the individual balloon catheters prohibits the use of multiple balloon catheters when treating multiple stenosis within the same vessel. Thus, to minimize the chance of oversizing the balloon when treating multiple stenosis within the same vessel, a physician may attempt to use a dilatation balloon which is noncompliant. However, as discussed previously, because such a balloon will permit little expansion beyond the balloon's rated or nominal diameter, the physician may not have available a balloon of sufficient size to safely treat the other stenosis within the same vessel.

Elastic stress response is determined by inflating a balloon to 5 bars at about 37° C. and measuring the balloon's diameter. The balloon is then inflated to a pressure of 10 bars in about 20 seconds and held for an additional 20 seconds at 37° C. The balloon's diameter is then measured. The internal pressure of the balloon is then decreased to 5 bars and the "new" 5 bar diameter of the balloons is determined. For this invention, the elastic stress response or repeatability is calculated using the following equation:

$$\text{Elastic Stress Response} = \left[\frac{\text{Balloon diameter at 5 bars after inflation to 10 bars}}{\text{Balloon diameter at intial 5 bar inflation}} - 1\right] \times 100$$

A balloon with maximum or complete elastic stress response permits the balloon, after being inflated to a pressure of 10 bars, to return to the same diameter it had at 5 bars prior to the inflation to the higher pressure. Such a balloon would have maximum repeatability, or an elastic stress response of 0.00. As the repeatability of the balloon decreases, the elastic stress response decreases and, as defined about, numerically becomes greater than 0.00. For example, balloons formed from polyolefin copolymers in the art have poor repeatability and a relatively low degree of elastic stress response and have a numerical elastic stress response of about 9.

It would be particularly desirable if a "compliant" balloon was able to possess an adequate degree of distensibility so that the balloon could be inflated to correspond to the size of the vessel being treated, while at the same time being highly elastic to ensure repeatable sizing and a high degree of elastic stress response so that the physician would know the balloon's "new" diameter at all inflation pressures prior to attempting to dilate multiple stenosis within the same vessel. This enhanced combination of properties would allow physicians to conduct dilation procedures in a safer manner in arteries where the physician requires balloon sizing not conveniently provided by "noncompliant" balloon products currently available in the art.

Another desirable characteristic of a balloon is flexibility. Improved flexibility will permit a balloon to traverse, not only occluded arteries, but also other obstructed or narrow body cavities and openings resulting in minimal damage to the vessel or cavity through which the balloon catheter is being navigated.

A further desirable property of a dilatation balloon, is the optical clarity of the finished balloon product. Although the optical clarity will not adversely affect a balloon's overall ability to dilate a stenosis or obstruction, most physicians will not use a balloon which has a cloudy apperance. The optical characteristics of a balloon or balloon catheter, therefore, must be taken into account when forming a balloon.

While the foregoing properties are desirable in balloons, these attributes are typically adversely affected by the sterilization process which all balloons and balloon catheters must be subjected to prior to their use in the human body. For example, when a balloon in the art is exposed to the increased temperature and humidity of a traditional sterilization process (e.g., high humidity, temperature of about 50–60° C., about 12% ethylene oxide and about 88% Freon™ for approximately 12–16 hours) the balloon tends to shrink which causes a corresponding increase in wall thickness. Moreover, this increase in wall thickness will adversely affect the folded profile of the sterilized balloon product. Furthermore, the distensibility of many balloons is adversely affected by the sterilization processes currently used in the art. Therefore, it is also desirable that the sterilization process used to treat balloons and balloon catheters provide adequate sterilization while at the same time not adversely affecting the physical characteristics of the finished balloon or balloon catheter product.

It has now been found that novel distensible balloons, particularly dilation balloons, can be formed by processing a polymeric material composed of polymer chains having sufficient regions of molecular structure with inter-molecular chain interaction to ensure the integrity and strength of the structure, as well as sufficient regions which permit sections of the polymer chains to "uncoil" to permit growth. The balloons contemplated by this invention (i) are sufficiently distensible (i.e., about 5 to about 20%) to allow treatment of various sized arteries, (ii) have a high degree of elastic stress response (i.e., less than about 5.00) which permits the physician to treat multiple stenosis within the same artery without having to be concerned with increasing balloon diameter after repeated inflations and (iii) have strength sufficient to treat hardened stenosis (i.e., greater than about 14,000 psi). The balloons formed using the process of this invention will have an overall advantageous combination of these physical properties i.e., distensibility, elastic stress response and tensile strength, superior to those exhibited by the "compliant" balloons currently available. It has also been found that these enhanced properties will not be adversely affected by subjecting the balloons and balloon catheters formed following the method or process of this invention to a novel sterilization process. This novel balloon forming process and novel sterilization process can be used regardless of whether the balloon is coated.

SUMMARY OF THE INVENTION

It is an object of this invention to provide a method or process for producing a balloon, preferably a dilatation balloon, which exhibits an improved overall combination of physical properties, such as distensibility, elastic stress response and strength, superior to those exhibited by "compliant" balloons currently known in the art.

It is further the object of this invention to provide a novel balloon and a novel balloon catheter in which the balloon exhibits an advantageous overall combination of distensibility, elastic stress response and strength which combination of properties will not be adversely affected by sterilization.

Still another object of this invention is to provide an improved sterilization procedure which will not adversely affect the distensibility, elastic stress response and strength of the balloons and balloons of the balloon catheters of this invention.

It is still a further object of this invention to provide a process which will ensure that the balloons formed will have improved optical clarity.

These objects, as well as others, which will become apparent from the description which follows, are achieved by forming these novel balloons and balloon catheters using the novel process of this invention from certain polymeric materials composed of polymer chains having regions of inter-molecular chain interaction separated by regions in which those individual portions of the polymer chains have the ability to uncoil or stretch. Therefore, the present invention includes (1) novel balloons and balloon catheters which have an improved overall combination of distensibility, elastic stress response and strength, (2) the process or method of forming balloons and balloon catheters from polymeric materials which will result in balloons and balloon catheters exhibiting these improved properties and (3) a novel sterilization process which will not adversely affect these enhanced properties.

The present invention contemplates balloons characterized by an improved overall combination of distensibility, elastic stress response and wall tensile strength made by the process comprising subjecting a parison, made of a block copolymer having polymer chains with regions of inter-molecular chain interaction separated by regions in which those individual portions of the polymer chains have the ability to stretch or uncoil to at least one axial stretch and at least one radial expansion step. The expanded parison is then subjected to a heat set step to provide the expanded parison and resulting balloon with thermal and dimensional stability. The invention also contemplates a novel sterilization process in which balloons and balloon catheters, after preconditioning, are exposed to ethylene oxide at a temperature of about 40° C. and a relative humidity of about 50–60% for approximately 6 hours. The balloons and balloon catheters are then subjected to an aeration step in which the ethylene oxide is allowed to dissipate. The novel sterilization process does not adversely affect the improved overall combination of properties exhibited by the balloons of this invention.

It should be understood that the foregoing description of the invention is intended merely to be illustrative and that other embodiments and modifications may be apparent to those skilled in the art without departing from the spirit and scope of the invention.

DETAILED DESCRIPTION OF THE INVENTION

The present invention provides for the first time "compliant" balloons, preferably dilatation balloons, which, because of the method or process used to form the balloons, as well as the polymeric materials used in the balloon forming process, produces balloons having a highly desirable combination of distensibility, elastic stress response and strength (i.e., distensibility of about 5 to about 20% and preferably in the range of about 6 to about 17%, elastic stress response of not greater than about 5.00 and preferably in the range of about 0.75 to about 4.00 and wall tensile strength of at least about 14,000 psi, preferably in the range of about 15,000 to about 40,000 psi and most preferably in the range of about 16,000 to about 30,000 psi). The invention also provides a uniquely method or process using a heat set step in the formation of the balloons of this invention which ensures that the balloons retain their distensibility and strength, and provides balloons with improved optical clarity. Moreover, the invention provides a novel sterilization process which will not adversely affect, to any significant degree, the enhanced combination of properties which are obtained using the novel balloon forming process of this invention.

The materials which may be used in this novel process or method include polymeric materials having a molecular structure which are composed of individual polymer chains having regions or zones of inter-molecular chain interaction separated by regions or zones in which those individual portions of the polymer chains have the ability to stretch or uncoil. The ability of regions or zones of individual polymer chains to uncoil permits the chains to move upon the application of stress. However because these zones are held in place or secured at either end by zones exhibiting inter-molecular chain interaction, the uncoiled portions return to their original position once the applied stress is removed.

These polymers can be considered to be comprised of polymer chains with individual regions of crystalline and amorphous material and can be referred to as "hard" and "soft" segments respectively. The individual polymer chains are able, to a substantial extent, to coil upon themselves and/or around each other in such a way that soft segments are associated with soft segments and hard segments with hard segments, thereby forming separate "domains" approximating soft and hard bodies of polymer, each exhibiting its own physical properties in varying degrees. The hard segments are comprised of regions which have significant inter-molecular chain interaction. This provides regions with increased strength and increased elastic stress response. In addition to providing strength, the hard segments are sufficiently rigid to permit the soft segments to stretch and uncoil which provides distensibility.

The ratio of hard to soft segments and individual chemical structure of the individual segments define the balloon's distensibility, elastic stress response and strength. Therefore, the polymeric material used in accordance with this invention should be have hard segments present in an amount sufficient to achieve a high degree of elastic stress response (i.e., not greater than about 5.00) and adequate wall tensile strength (i.e., at least about 14,000 psi), while at the same time having an adequate amount of soft segments to ensure that the balloon is also distensible (i.e., about 5 to about 20%).

Examples of polymeric materials which have these alternating zones or regions and which may be used in forming the balloons and balloon catheters of this invention include block copolymers, and physical mixtures of different polymers. Examples of block copolymers which may be used include polyester block copolymers, polyamide block copolymers and polyurethane block copolymers. Examples of the mixtures which may be used include mixtures of nylon and polyamide block copolymers and polyethylene terephthalate and polyester block copolymers. The preferred block copolymer which can be used in accordance with the process of this invention is polyurethane block copolymer. This preferred polymer may be made, for example, by a reaction between a) an organic diisocyanate;
b) a polyol; and
c) at least one chain extender.

The preferred polyurethanes which can be used in this invention may be varied by using different isocyanates and polyols which will result in different ratios of hard to soft segments as well as different chemical infractions within the individual regions of the polymer.

An example of the most preferred polyurethane is manufactured by The Dow Chemical Company and marketed under the trade name PELLETHANE 2363-75D. This raw material has a Shore Hardness of about 74 D, a specific gravity of about 1.21, a tensile modulus of about 165,000 psi, a flexural modulus of about 190,000 psi, an ultimate tensile strength of about 6,980 psi and an ultimate elongation of about 250%.

In accordance with this invention, the balloons are formed from a thin wall parison of a polymeric material, preferably made of a polyurethane block copolymer, which is treated in accordance with the process of this invention. The novel process contemplated by this invention employs a heat set step which will provide a balloon with temperature and dimensional stability. This stability results from the fact that the balloon is heated about the temperature using in the balloon forming process so that the orientation resulting from the processing conditions is "locked" into position.

The balloons and balloon catheters of this invention may be formed using a mold which can be provided with a heating element. The mold receives a tubular parison made of a polymeric material of the type used in accordance with the present invention. The ends of the parison extend outwardly from the mold and one of the ends is sealed while the other end is affixed to a source of inflation fluid, typically nitrogen gas, under pressure. Clamps or "grippers" are attached to both ends of the parison so that the parison can be drawn apart axially in order to axially stretch the parison while at the same time said parison is capable of being expanded radially or "blown" with the inflation fluid. The radial expansion and axial stretch step or steps may be conducted simultaneously, or depending upon the polymeric material of which the parison is made, following whatever sequence is required to form a balloon. Failure to axial stretch the parison during the balloon forming process will result in result in a balloon which will have an uneven wall thickness and which will exhibit a wall tensile strength lower than the tensile strength obtained when the parison is both radially expanded and axially stretched.

The polymeric parisons used in this invention are preferably drawn axially and expanded radially simultaneously within the mold. To improve the overall properties of the balloons formed, it is desirable that the parison is axially stretched and blown at temperatures above the glass transition temperature of the polymeric material used. This expansion usually takes place at a temperature between about 80 and about 150° C. depending upon the polymeric material used in the process.

In accordance with this invention, based upon the polymeric material used, the parison is dimensioned with respect to the intended final configuration of the balloon. It is particularly important that the parison have relatively thin walls. The wall thickness is considered relative to the inside diameter of the parison which has wall thickness-to-inside diameter ratios of less than 0.6 and, preferably between 0.57 and 0.09 or even lower. The use of a parison with such thin walls enables the parison to be stretched radially to a greater and more uniform degree because there is less stress gradient through the wall from the surface of the inside diameter to the surface of the outside diameter. By utilizing a parison which has thin walls, there is less difference in the degree to which the inner and outer surfaces of the tubular parison are stretched.

The parison is drawn from a starting length L1 to a drawn length L2 which preferably is between about 1.10 to about 6 times the initial length L1. The tubular parison, which has an initial diameter ID1 and an outer diameter OD1 is expanded by the inflation fluid emitted under pressure to the parison to an internal diameter ID2 which is preferably about 6 to about 8 times the initial internal diameter ID1 and an outer diameter OD2 which is about equal to or preferably greater than about 3 times the initial outer diameter OD1. The parison is preferably subjected to between 1 and 5 cycles during which the parison is axially stretched and radially expanded with an inflation pressure of between about 100 and about 500 psi. Nitrogen gas is the preferable inflation fluid for the radial expansion step.

After the desired number of "blow" cycles have been completed, the expanded parison is subjected to a heat set or thermoforming step during which the expanded parison, still subjected to an inflation pressure of about 100 to about 500 psi, is held at a temperature above the temperature at which the balloon was axially stretched and radially expanded, but below the melting temperature of the polymeric material from which the parison was formed. This higher temperature induces crystallization and "freezes" or "locks" the orientation of the polymer chains which resulted from axially stretching and radially expanding the parison. The temperatures which can be used in this heat set step are therefore dependent upon the particular polymeric material used to form the parison and the ultimate properties desired in the balloon product (i.e., distensibility, strength and compliancy). The heat set step ensures that the expanded parison and the resulting balloon will have temperature and dimensional stability. After the heat set step is completed, the mold is cooled to about 37° C. The finished balloon will typically obtain its rated or nominal diameter when inflated to a pressure of about 5 to about 8 bars depending upon the polymeric material used to form the balloon. The balloon thus formed may be removed from the mold, and affixed to a catheter.

For example, if the parison is formed from the polyurethane marketed by The Dow Chemical Company under the trade name PELLETHANE 2363-75D and axially stretched and radially expanded at a temperature of about 90–100° C., the heat set step would preferably be conducted at about 105–120° C. If this step was conducted at temperatures much above about 120° C., the tensile strength of the resulting polyurethane balloon would decrease significantly. Moreover, if the heat set step was conducted at temperatures significantly higher than 120° C., the distensibility of the resulting polyurethane balloon would also be adversely affected. However, if the heat set was conducted at temperatures below about 100° C., the polyurethane balloons formed would be dimensionally unstable resulting in balloons with uneven wall thicknesses. Additionally, the lower heat set temperature would result in balloons exhibiting physical properties which would more likely be adversely affected during sterilization. Finally, a balloon having a cloudy appearance, a property which physicians find particularly undesirable, would be another consequence of using a low heat set temperature.

It should be noted that some adjustment in the foregoing axial stretch and radial expansion ratios, as well as the expansion and heat set temperatures may be necessary to take into account the difference in physical properties between the polyurethane block copolymer exemplified above and any other polymeric materials which can be used in accordance with this invention.

In order to preserve a balloon's distensibility, elastic stress response, wall tensile strength and improved optical clarity, the balloon formed must also be subjected to the novel sterilization process contemplated by the invention. For example, if a sterilization process which is currently available in the art is used (e.g., high relative humidity at about 50–60° C. in the presence of about 12% ethylene oxide and about 88% Freon™ for about 9–16 hours), the elastic stress response, distensibility and the strength of the balloons contemplated by this invention would be adversely affected. When the novel low temperature, low humidity, ethylene oxide sterilization process of this invention is used to sterilize the balloons and balloon catheters of this invention, the elastic stress response, distensibility and strength of the balloons are not adversely affected to any significant degree.

The novel low temperature, low humidity sterilization process consists of exposing the balloon or balloon catheter to a preconditioning step at temperature about 35 to about 45° C. and a relative humidity of about 55% for about 15 hours. The balloon or balloon catheter is then treated at a temperature of about 35 to about 45° C. and a relative humidity of about 55% with ethylene oxide, preferably in a cincentrtion of about 100%. After being exposed to ethylene oxide for about 6 hours, the products are aerated and kept at a temperature of about 35 to about 45° C. for about 22 hours, in order to permit the ethylene oxide to dissipate. The sterilized balloon products are now ready for human use.

The sterilization process cannot, however, be conducted above the heat set temperature since this would relieve the orientation of the polymer chains which was "locked" into place during heat set process. The sterilization process appears to be an important factor in determining the final physical characteristics of the balloons and balloon catheters of this invention. Therefore, the novel sterilization process is necessary to ensure a clinically useful and sale finished balloon and balloon catheter with an overall advantageous combination of physical properties (i.e., distensibility, elastic stress response and wall tensile strength) superior to those exhibited by the "complaint" balloons of the prior art.

EXAMPLE 1

A parison was made from the polyurethane manufactured by The Dow Chemical Company and marketed under the trade name PELLETHANE 2363-75D. This material has a Shore Hardness of about 74D, a specific gravity of about 1.21, a tensile strength of about 165,000 psi, a flexural modulus of about 190,000 psi, an ultimate tensile strength of about 6,980 psi and an ultimate elongation of about 250%. The parison was sealed at one end while the other end was attached to the source of the pressurized inflation fluid, in this example nitrogen gas. Clamps were attached to each end of the parison. The mold was then heated to an operating temperature of about 90–100° C., while the parison was pressurized with nitrogen gas at about 290 psi and held for about 70 seconds.

The pressure was then relieved and the parison was subjected to a series of radial expansion or "blow" cycles. During each radial expansion or "blow" cycle, the parison was also axially stretched while being pressured at about 290 psi for about 5 seconds. The pressure was then releived, and the parison was subject to continued axial stretching for about 5 seconds. The parison was then subject to another expansion cycle. After three expansion or blow cycles, the original outer diameter had increased from 0.035 inches to 0.1181 inches.

The expanded parison was then pressurized to about 190 psi and was subjected to a heat set step during which the expanded parision was held for about 75 seconds at a temperature of about 110° C. The pressurized balloon was then cooled to about 37° C. for about 30 seconds. The pressure was then relieved and the balloon was held vertically in the mold at about 37° C. for about 120 seconds to minimize balloon curvature. The balloon was released from the clamps and removed from the mold. The balloon, having a nominal or rated diameter of 3.0 mm, displayed an improved overall combination of distensibility, elastic stress response and strength when compared to "compliant" balloons of the art and was ready for attachment to a catheter.

EXAMPLE 2

The balloons formed following the process set forth in Example 1 were placed in a sterilization chamber and kept at a temperature of about 40° C.±3° C. and a relative humidity of about 55% for about 15 hours. The balloons are kept at a temperature of about 40° C.±3° C. and were then treated with 100% ethylene oxide. After being exposed to the ethylene oxide for about 6 hours, the balloons were removed from the sterilization chamber and held at a temperature of about 40° C.±3° C. and ambient relative humidity for about 22 hours in order to dissipate the ethylene oxide. At this point, the balloons were sterilized and ready for human use.

EXAMPLE 3

The effect which the novel sterilization process of this invention has on the balloons formed using the balloon forming process contemplated by this invention are demonstrated below. Balloons with a nominal diameter of 3.0 mm were formed from polyurethane following the process described in Example 1. One group of balloons was subjected to the sterilization process contemplated by this invention and described previously in Example 2, sterilization process contemplated by this invention and described previously in Example 2, while the other group of balloons were subjected to a sterilization process currently used in the art.

In that sterilization process (referred to in this Example as "traditional sterilization process"), the balloons were preconditioned at a temperature of about 43° C. and a relative humidity of about 60% for about 24 hours. The balloons were then treated with about 12% ethylene oxide and 88% Freon™ at a temperature of about 54° C. After being treated with the ethylene oxide mixture for about 9 hours, the balloons are removed from the sterilization chamber and kept at a temperature of about 38° C. for about 22 hours.

The average wall tensile, burst pressure, elastic stress response and distensibility (i.e., radial expansion) of both sets of balloons were compared below.

| Sterilization Conditions | Average Wall Tensile Strength (psi) | Average Burst Pressure (atm) | Average Elastic Stress Response | Average Distensibility |
| --- | --- | --- | --- | --- |
| novel sterilization conditions described in Example 2 | 16,297 | 22.0 | 3.38 | 9.4% |
| traditional sterilization process | 14,497 | 22.6 | 10.29* | 20.2% |

*The balloons used to determine elastic stress response for this comparison with the novel sterilization conditions were treated with 100% ethylene oxide rather than 12% ethylene oxide and 88% Freon ™. All other temperature and time conditions were the same.

EXAMPLE 4

The following example demonstrates the importance of the heat set step. Three dilatation balloons with a nominal or rate diameter of 3.0 mm, were formed form polyurethane following the process described in Example 1. The average burst pressure, distensibility and wall tensile strength of balloons formed using different heat set temperatures are compared. The burst pressure and distensibility were determined at 37° C.

| Heat set T Temperature (° C.) | Average Wall Tensile Strength (psi) | Average Burst Pressure (atm) | Average Distensibility |
|---|---|---|---|
| 160 | 14,712 | 12.8 | 10.26% |
| 132 | 23,364 | 20.6 | 5.81% |
| 118 | 25,346 | 22.2 | 5.96% |

EXAMPLE 5

The following example demonstrates the improved elastic stress response or "repeatability" which can be obtained by the balloons and balloon catheters formed following the process contemplated by this invention. In this example, dilatation balloons with a nominal or rated diameter of 3.0 mm were formed from polyurethane following the process described in Example 1. A number of polyurethane balloons were sterilized following the process previously described in Example 3 (referred to as "traditional sterilization" in this Example). Another group of polyurethane balloons were sterilized using the novel sterilization process contemplated by this invention and previously described in Example 2. The elastic stress response of these polyurethanes balloons were compared with the elastic stress response of the other sterilized 3.0 mm balloons known in the art.

| Balloon | Average Diameter at Initial 5 Bar Inflation | Average Diameter at 5 Bars After A Single Inflation to 10 Bars | Average Elastic Stress Response |
|---|---|---|---|
| Polyurethane (sterilization described in Example 2) | 2.96 | 3.06 | 3.38 |
| Polyurethane (traditional sterilization) | 2.72 | 3.00 | 10.29 |
| Polyethylene terephthalate | 3.02 | 3.04 | 0.66 |
| Cross-linked polyethylene | 2.98 | 3.11 | 4.36 |
| Cross-linked polyolefin-ionomer | 2.93 | 3.19 | 8.87 |

EXAMPLE 6

The following example demonstrates the improved overall combination of distensibility, elastic stress response and wall tensile strength obtained by forming balloons by using the process of this invention. Balloons with a nominal or rated diameter of 3.0 mm were formed from polyurethane following the process described in Example 1. The average elastic stress response, distensibility and wall tensile strength of those polyurethane balloons are compared with properties of other 3.0 mm balloons of the art.

| Balloon | Average Elastic Stress Response | Average Distensibility | Average Wall Tensile Strength (psi) |
|---|---|---|---|
| Polyurethane | 3.38 | 9.4% | 16,297 |
| Polyethylene terephthalate | 0.66 | 3.26% | 62,081 |
| Cross-linked polyethylene | 4.36 | 9.67% | 8,868 |
| Cross-linked polyolefin-ionomer | 8.87 | 14.64% | 6,793 |

What is claimed is:

1. A balloon characterized by an improved overall combination of distensibility, elastic stress response and wall tensile strength made by the process comprising:
   a. providing a parison of a block copolymer composition including a block copolymer having regions of (i) hard segments defined by regions of inter-molecular chain interaction separated by (ii) soft segments defined by regions in which individual polymer chains have the ability to uncoil, said parison having a predetermined initial outer diameter, a predetermined initial wall thickness and a predetermined initial length;
   b. subjecting said parison to at least one axial stretch step and at least one radial expansion step at temperature $T_1$ which is below the melting temperature of said block copolymer composition to increase the diameter and length of said parison to at least three times the initial diameter and at least two times the initial length and to decrease the initial wall thickness to at least 20% of the initial wall thickness to form an expanded parison; and
   c. heating said expanded parison to a temperature of $T_2$ which is above $T_1$ but below the melting temperature of said block copolymer composition; and
   d. cooling said expanded parison to produce said balloon; wherein the ratio of said hard segments to said soft segments provides said balloon with (a) an elastic stress response not greater than 5.00, (b) a wall tensile strength of at least about 14,000 psi and (c) a distensibility of between about 5% and about 20%.

2. The balloon according to claim 1 wherein said radial expansion step is conducted while said parison is simultaneously subjected to said axial stretch step.

3. The balloon according to claim 1 wherein said axial stretch and radial expansion steps are conducted at temperature $T_1$ which is greater than the glass transition temperature of said block copolymer.

4. A balloon according to claim 1 wherein said block copolymer is selected from the group consisting of polyester block copolymers, polyamide block copolymers, polyurethane block copolymers, a mixture of nylon and polyamide block copolymers and a mixture of polyethylene terephthalate and polyester block copolymers.

5. A balloon according to claim 1 wherein said balloon has a distensibility of about 6 to about 17%, an elastic stress response of about 0.75 to about 4.00 and a wall tensile strength of about 16,000 to about 30,000 psi.

6. A balloon according to claim 5 wherein $T_1$ is about 90–100° C. and $T_2$ is about 110–120° C.

7. A balloon according to claim 1 wherein said block copolymer is a polyurethane having a Shore Hardness of about 74D, a specific gravity of about 1.21, a tensile modulus of about 165,000 psi, a flexural modulus of about 190,000 psi, an ultimate tensile strength of about 6,980 psi and an ultimate elongation of about 250%.

8. A balloon catheter comprising the balloon of claim 1.

9. A balloon for a balloon dilatation catheter comprising: a radially expanded and axially stretched tubular member formed of a block copolymer composition including a block copolymer having regions of (I) hard segments defined by regions of inter-molecular chain interaction separated by (II) soft segments regions in which individual polymer portions of chains have the ability to uncoil, wherein the ratio of said hard segments to said soft segments is such as to provide said balloon with (a) an elastic stress response not greater than about 5.00, (b) a wall tensile strength of at least about 14,000 psi and (c) a distensibility of between about 5% and about 20%.

10. A balloon according to claim 9 wherein said block copolymer is selected from the group consisting of a polyester block copolymer, a polyamide block copolymer, a polyurethane block copolymer, a mixture of a nylon and a polyamide block copolymer and a mixture of polyethylene terephthalate and a polyester block copolymer.

11. A balloon according to claim 10 wherein said balloon had a distensibility of about 6 to about 17%, an elastic stress response of between about 0.75 to about 4.00 and a wall tensile strength of about 16,000 to about 30,000 psi.

12. A balloon according to claim 10 wherein said block copolymer is a polyurethane block copolymer.

13. A balloon according to claim 12 wherein said polyurethane block copolymer has a Shore Hardness of about 74D, a specific gravity of about 1.21, a tensile modulus of about 165,000 psi, a flexural modulus of about 190,000 psi, an ultimate tensile strength of about 6,980 psi and an ultimate elongation of about 250%.

14. A balloon according to claim 9 wherein said balloon had a distensibility of about 6 to about 17%, an elastic stress response of between about 0.75 to about 4.00 and a wall tensile strength of about 16,000 to about 30,000 psi.

* * * * *